United States Patent
Hamon et al.

(10) Patent No.: US 10,729,158 B2
(45) Date of Patent: Aug. 4, 2020

(54) NON-MEDICINAL FOOD ADDITIVE FOR ANIMALS, SUPPLEMENTED FOOD CONTAINING SAME AND METHOD FOR IMPROVING ANIMAL GROWTH

(71) Applicants: Institut Regional Des Materiaux Avances (IRMA), Ploemeur (FR); Invivo NSA, Saint-Nolff (FR)

(72) Inventors: Christian Hamon, Saint-Nazaire (FR); Alain Guyonvarch, Vannes (FR)

(73) Assignee: P&A France, Saint-Nolff (FR)

( * ) Notice: Subject to any disclaimer, the term of this patent is extended or adjusted under 35 U.S.C. 154(b) by 342 days.

(21) Appl. No.: 14/288,993

(22) Filed: May 28, 2014

(65) Prior Publication Data
US 2014/0272001 A1 Sep. 18, 2014

Related U.S. Application Data

(63) Continuation of application No. 11/918,396, filed as application No. PCT/EP2006/061530 on Apr. 11, 2006, now abandoned.

(30) Foreign Application Priority Data

Apr. 13, 2005 (FR) ...................................... 05 03671

(51) Int. Cl.
| | |
|---|---|
| A23K 1/17 | (2006.01) |
| A23K 20/174 | (2016.01) |
| A23K 50/70 | (2016.01) |
| A23K 50/80 | (2016.01) |
| A23K 50/30 | (2016.01) |
| A23K 20/28 | (2016.01) |
| A23K 50/50 | (2016.01) |
| A23K 50/10 | (2016.01) |
| A23K 20/20 | (2016.01) |
| A23K 50/75 | (2016.01) |

(52) U.S. Cl.
CPC ............ *A23K 20/174* (2016.05); *A23K 20/28* (2016.05); *A23K 20/30* (2016.05); *A23K 50/10* (2016.05); *A23K 50/30* (2016.05); *A23K 50/50* (2016.05); *A23K 50/70* (2016.05); *A23K 50/75* (2016.05); *A23K 50/80* (2016.05)

(58) Field of Classification Search
None
See application file for complete search history.

(56) References Cited

U.S. PATENT DOCUMENTS

| | | | |
|---|---|---|---|
| 4,610,882 | A | 9/1986 | Laurent et al. |
| 4,970,080 | A | 11/1990 | Laurent et al. |
| 5,314,852 | A | 5/1994 | Klatte et al. |
| 6,215,037 | B1 | 4/2001 | Padin et al. |
| 2006/0292242 | A1 | 12/2006 | Hraschan et al. |

FOREIGN PATENT DOCUMENTS

| | | | |
|---|---|---|---|
| CN | 1346600 | 5/2002 | |
| EP | 0 288 063 B1 | 4/1988 | |
| EP | 0 270 129 | 6/1988 | |
| JP | 59-203450 | 11/1984 | |
| JP | 59-203450 A | * 11/1984 | ............ A23K 1/175 |
| JP | 02084957 | 3/1990 | |
| JP | 04021517 | 1/1992 | |
| JP | 2005-052126 | 3/2005 | |
| WO | WO 03/072116 A1 | 9/2003 | |
| WO | WO 03/077674 A1 | 9/2003 | |

OTHER PUBLICATIONS

Top et al., *Silver, zinc, and copper exchange in a Na-clinoptilolite and resulting effect on antibacterial activity*, 27 Applied Clay Science 13-19 (2004).
Rakic et al., "CO interaction with zeolites studied by TPD and FTIR: transition-metal ion-exchanged FAU-type zeolites," Microporous and Mesoporous Materials, Elsevier Science Publishing, New York, US, vol. 27, No. 1, Jan. 1999, pp. 27-39.
Förster et al., "Investigations of coke deposits formed during deep oxidation of benzene over Pd and Cu exchanged Y-type zeolites," Applied Catalysis A: General, Elsevier Science Publishing, Amsterdam, NL, vol. 153, No. 1-2, May 29, 1997, pp. 31-41.
Database WPI, Section Ch, Week 200205, Derwent Publications Ltd., London, GB, Class B05, AN 2002-034962, XP002348349 & CN 1310945 A (Chen S) Sep. 5, 2001 abstract, example 5; table 2.
Inoue et al., "Bactericidal activity of Ag-zeolite mediated by reactive oxygen species under aerated conditions," Journal of Inorganic Chemistry, Elsevier Science Publishing, vol. 92, No. 1, Sep. 30, 2002, pp. 37-42.

(Continued)

*Primary Examiner* — David Browe
(74) *Attorney, Agent, or Firm* — Panitch Schwarze Belisario & Nadel LLP

(57) ABSTRACT

This invention relates to a non-medical food additive that is an animal growth promoter containing 99% pure zeolite partially or totally exchanged with a $C^{m+}$ cation (in other words a synthetic zeolite) with the general formula I below:

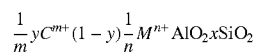

$$\frac{1}{m} y C^{m+} (1-y) \frac{1}{n} M^{n+} AlO_2 x SiO_2$$

in which x is greater than 1 and advantageously between 1 and 15;
$M^{n+}$ represents an alkaline or alkaline earth exchangeable ion, advantageously $Na^+$, $K^+$, $Ca^{2+}$ or $Li^+$;
n is between 1 and 2;
y is the exchange rate and is between 0.001 and 1;
$C^{m+}$ is a metallic cation chosen from among copper $Cu^{2+}$, silver $Ag^+$ or zinc $Zn^{2+}$;
m is between 1 and 2.

It also relates to an additive premix and a supplemented food containing it and a method of improving the growth of animals.

21 Claims, 1 Drawing Sheet

(56) References Cited

OTHER PUBLICATIONS

Matsumura et al., "Mode of Bactericidal Action of Silver Zeolite and Its Comparison with That of Silver Nitrate," Applied and Environmental Microbiology, Washington, DC, US, vol. 69, No. 7, Jul. 2003, pp. 4278-4281.

Hu et al., "Effects of Copper-Bearing Montmorillonite on Growth Performance and Digestive Function of Growing Pigs," Asian-Australasian Journal of Animal Sciences, vol. 17, No. 11, 2004, pp. 1575-1581.

Xia et al., "Effects of Copper-Bearing Montmorillonite on Growth Performance, Digestive Enzyme Activities, and Intestinal Microflora and Morphology of Male Broilers", Metabolism and Nutrition, 2004 Poultry Science 83, pp. 1868-1875.

Xu et al., "Effects of Cu(II)-exchanged Montmorillonite on Growth Performance, Intestinal Microflora, Bacterial Enzyme Activities and Morphology of Broilers," Asian-Aust. J. Anim. Sci. 2003, vol. 16, No. 11, pp. 1673-1679.

Xia et al., Effects of Copper-bearing Montmorillonite (Cu-MMT) on Escherichia coli and Diarrhea on Weanling Pigs, Asian-Aust. J. Anim. Sci. 2004, vol. 17, No. 12, pp. 1712-1716.

Cik et al., "Study of fungicidal and antibacterial effect of the Cu(II)-complexes of thiophene oligomers synthesized in ZSM-5 zeolite channels," Chemosphere vol. 44 (2001), pp. 313-319.

Hu et al., "Effects of $Cu^{2+}$-exchanged montmorillonite on growth performance, microbial ecology and intestinal morphology of Nile tilapia (Oreochromis niloticus)," Aquaculture vol. 270 (2007), pp. 200-206.

Jo et al., "Combined treatment with silver ions and organic acid enhances growth-inhibition of Escherichia coli O157:H7," Food Control, vol. 18, No. 10, Oct. 2007, pp. 1235-1240.

Yamamoto et al., "Preparation of anti-bacterial zeolites and their anti-bacterial effects," JPN J Food Chem., vol. 9 No. 3, 2002 (abstract).

Hu et al., "Antibacterial effect of $Cu^{2+}$-exchanged montmorillonite on Aeromonas hydrophila and discussion on its mechanism," Veterinary Microbiology, vol. 109, Issues 1-2, Aug. 10, 2005, pp. 83-88.

International Search Report corresponding to PCT/EP 2006/061530, dated Sep. 12, 2006, 4 pages.

Xia, Effects of Copper-Bearing Montmorillonite on Growth Performance, Digestive Enzyme Activities, and Intestinal Microflora and Morphology of Male Broilers, 83 Poultry Science 1868-1875 (2004).

\* cited by examiner

NON-MEDICINAL FOOD ADDITIVE FOR ANIMALS, SUPPLEMENTED FOOD CONTAINING SAME AND METHOD FOR IMPROVING ANIMAL GROWTH

CROSS-REFERENCE TO RELATED APPLICATIONS

This application is a Continuation Application of U.S. patent application Ser. No. 11/918,396, filed on Nov. 21, 2008, which is a U.S. National Stage pursuant to 35 U.S.C. § 371 of International Patent Application PCT/EP2006/061530, filed on Apr. 11, 2006, and published as WO 2006/108845 on Oct. 19, 2006, which claims priority to French Patent Application 05/03671, filed on Apr. 13, 2005, all of which are incorporated herein by reference in their entireties for all purposes.

This invention relates to a non-medical food additive promoting animal growth, supplemented foods containing this additive and a method of improving animal growth.

"Growth promoter" food additives have been used for a long time to improve zootechnical performances of animals (mammals, birds or fish). These products are obtained either by fermentation or by chemical synthesis or by extraction from plants.

Until now, antibiotics were used extensively as growth promoters. However, regulations have changed and have become increasingly strict and antibiotics will no doubt be prohibited in animal food in the near future.

Some non-medical growth promoters already exist.

Growth promoters include clays containing copper such as montmorillonite (flaky clay) have been suggested (Xia et al. 2004 Poultry Science 83: 1868-1875, Xu et al., *Asian-Aust. J. Anim. Sci.* 2003. Vol 16, No. 11: 1673-1679, Xia et al., *Asian-Aust. J. Anim. Sci.* 2004. Vol 17, No. 12: 1712-1716 and Hu et al., *Asian-Aust. J. Anim. Sci.* 2004. Vol 17, No. 11: 1575-1581). However, the doses necessary to promote growth are very high (1.5 g/kg of food, in other words about 1500 ppm).

This creates a problem in terms of the transport cost of this promoter or the food containing it. Furthermore, the addition of 1500 ppm of inert mineral can induce sequestration of some trace elements. Furthermore, the copper content of the exchanged montmorillonite is 2.45%, which means 36.75 ppm of added copper in the ration, and exceeds the maximum copper content allowable by CEE regulations in food for most species (copper contained in raw materials+ added copper).

Therefore, at the moment there is a real need for a non-medical animal growth promoter that can be active in a small proportion and therefore easily transportable.

Surprisingly, the inventors have discovered that a zeolite exchanged with copper can be used as a growth promoter for animals at doses much less than 1500 ppm.

Thus, this invention relates to a non-medical food additive that is an animal growth promoter containing 99% pure zeolite (in other words a synthetic zeolite) partially or totally exchanged with a $C^{m+}$ cation with the general formula I below:

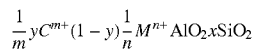

in which x is greater than 1 and advantageously between 1 and 15, and advantageously between 1 and 10;

$M^{n+}$ represents an alkaline or alkaline earth exchangeable ion, advantageously $Na^+$, $K^+$, $Ca^{2+}$ or $Li^+$ and advantageously $Na^+$;

n is between 1 and 2;

y is the exchange rate and is between 0.001 and 1;

$C^{m+}$ is a metallic cation chosen from among copper $Cu^{2+}$, silver $Ag^+$ or zinc $Zn^{2+}$, and advantageously chosen from among copper $Cu^{2+}$ and silver $Ag^+$;

m is between 1 and 2.

In one advantageous embodiment, y is between 0.001 and 0.80, advantageously between 0.01 and 0.80, advantageously between 0.1 and 0.80, advantageously between 0.1 and 0.75; and even more advantageously between 0.1 and 0.5.

Synthetic zeolites, in other words approximately 99% pure zeolites, are crystallised micro porous silicates for which channel and cavity sizes vary between 3 and 13 Å, depending on the structure. They are in the form of a powdery powder, the size of crystals being a few microns on average, and advantageously between 1 and 2 microns.

x is the Si/Al ratio. In the normal state, there is water (capillary condensation) in the pores of a zeolite. Water can be eliminated by increasing the temperature. Due to their tetrahedral structure (chaining of $SiO_4$ and $AlO_4$ tetrahedrons with oxygen in common, which leads to a negative charge on each Aluminium ($AlO_2^-$) compensated by a $M^{n+}$ cation), the zeolites are cation exchangers in which the $M^{n+}$ cation can be replaced (usually $Na^+$ (n=1) after synthesis) by other $C^{m+}$ cations. These exchange operations and the manner in which they are controlled are known to those skilled in the art.

In general, in order to make these exchanges, zeolite is put into suspension while stirring in an aqueous solution of a metallic salt for which it is required to introduce the $C^{m+}$ cation (for example $Cu^{++}$ in the form of a sulphate (m=2)) by exchange in zeolite.

The exchange reaction is managed by the mass action law. Considering a zeolite in its sodic form ($M^{n+}=Na^+$) with exchange by a cation $C^+$ (m=1), the reaction is written:

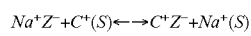

S: Solution
Z: Zeolite

This reaction is in equilibrium and the equilibrium constant Kp depends only on the temperature.

Due to the equilibrium concept, the exchange is usually incomplete, there is still some $Na^+$ and $C^+$ in the zeolites distributed on the different cationic sites.

$M^+$ can also be exchanged by bivalent cations (for example $C^{m+}=Cu^{++}$) or trivalent cations but in this case, 1 $Cu^{++}$ obviously replaces $2Na^+$ if $M^{n+}=Na^+$ (n=1) and $C^{m+}=Cu^{++}$ (m=2).

The parameters that will influence the exchange and therefore the content of $C^{m+}$ cations after the exchange will be the temperature, the metallic salt concentration in the solution and the solution volume/weight ratio (V/P) of zeolite; time has an influence if equilibrium is not reached.

Advantageously, the zeolite according to this invention is chosen from among type A zeolite, type X zeolite, type Y zeolite, mordenite, ferrierite, beta zeolite and pentasil type structures. Advantageously, it is chosen from among type A zeolite, type X zeolite, type Y zeolite, and advantageously it is a zeolite with a faujasite structure and even better it is type Y zeolite.

In particular, x=1 for a type A zeolite. Advantageously, type A zeolite is chosen from the group composed of zeolite 3A, 4A or 5A.

Advantageously, x is equal to 1.25 for type X zeolites. Advantageously, x is equal to 2.6 for a type Y zeolite. Even more advantageously, x is equal to 5.5 for a mordenite. In particular, x is equal to 13.5 for a zeolite with a pentasil type structure. Advantageously, x is equal to 8.8 for a ferrierite.

Advantageously, the $C^{m+}$ metallic cation of the zeolite according to this invention is copper $Cu^{2+}$.

In another advantageous embodiment, the zeolite according to this invention is of type Y, the metallic cation $C^{m+}$ is copper $Cu^{2+}$ and the zeolite contains between 1 and 12.5% by weight of copper as a proportion of the total weight of zeolite, advantageously between 3 and 9% and even better between 5 and 6% by weight. Advantageously, the $M^{n+}$ ion is $Na^+$.

In one advantageous embodiment, the zeolite according to this invention is of type Y, the metallic cation $C^{m+}$ is silver $Ag^+$ and the zeolite contains between 1 and 33% by weight of silver as a proportion of the total weight of zeolite, advantageously between 10 and 25%, advantageously between 13 and 25% and advantageously about 20%.

In one particular embodiment of the invention, the zeolite according to this invention is of type Y, the metallic cation $C^{m+}$ is zinc $Zn^{2+}$ and the zeolite contains between 1 and 13% by weight of zinc as a proportion of the total weight of zeolite, preferably between 3 and 8% by weight of zinc as a proportion of the total weight of zeolite, and advantageously about 5% by weight of zinc.

Advantageously, the food additive according to this invention is for use for feeding farm animals or pets, advantageously chosen from among porcines (particularly pigs), bovines, ovines, goats, poultry (particularly chickens and turkeys), rabbits, fish and birds.

In most cases and depending on the purpose, the growth promoter is administered to the animals orally. In selecting the individual forms of administration, the specific characteristics of each species and the age of the animals must be taken into account.

Furthermore, in practice each animal must receive the necessary dose of growth promoter and no inevitable losses must take place.

Food containing the growth promoter may indifferently be presented in any normal form known in breeding.

Thus, food may be simple or compound, complete or complementary food (trace elements, enzymes, acidifiers, aromatic substances and aperitives, vitamins, etc.).

If young animals are always fed by their mother, the growth promoter is preferably injected directly into the throat in the form of a suspension or a solute.

For calves, the growth promoter may be administered in the form of a milk suspension. It is also possible to add it into drinking water. For animals that already eat solid food, the growth promoter may be mixed with food. Depending on the animal species, this food may be chosen from among cereals, products and by-products; oil bearing seeds and fruit and their products and by-products; leguminous plant seeds and their products and by-products, tubers and roots and their products and by-products; other seeds and fruit and their products and by-products; fodder including roughage; other plants and their products and by-products; dairy products; land animal products; fish and other marine animals, and their products and by-products; minerals; vitamins alone or mixed.

One preferred form of administration is cubes or granules that, in addition to the growth promoter, contain normal constituents of food of the animal in question, chosen from among cereals, products and by-products; oil bearing seeds and fruit and their products and by-products; leguminous plant seeds and their products and by-products, tubers and roots and their products and by-products; other seeds and fruit and their products and by-products, fodder including roughage; other plants and their products and by-products; dairy products; land animal products; fish and other marine animals, and their products and by-products; minerals; vitamins alone or mixed.

The composition may be administered to fish in the form of capsules with a diameter of 1 to 7 mm that are insoluble in water at ambient temperature. Another possibility is administration of food granules containing fat in which the growth promoter is insoluble or only slightly soluble.

Doses of growth promoter used may vary depending on the species, the age, the animal ingestion level and to a certain extent depending on the required effect. The specialist should use systematic tests to determine the optimum dose for each use. Advantageously, within the framework of this invention, the quantity of zeolite present according to this invention is between 5 and 200 ppm as a proportion of the total weight of the food, and advantageously between 5 and 100 ppm, and even better between 5 and 80 ppm, even better between 5 and 20 ppm or equal to approximately 10 mm.

Advantageously, recommendations for the administration of zeolite according to this invention are 0.8 to 1.2 mg/kg of live weight (PV) x day for porcines and 0.6 to 0.9 mg/kg PV x day for poultry.

Thus, the "growth promoter" food additive according to this invention may be in pure form or it may be mixed with various allowable supports and/or other additives.

Advantageously, due to the low incorporation rate necessary to obtain the growth promoter effect, the zeolite according to this invention is not incorporated in its existing form into food, but through a premix of additives.

Therefore, this invention relates to a premix of non-medical growth promoter food additive for animals, characterised in that it contains a food additive according to this invention on a support and/or in combination with at least another animal food additive. This other food additive may be non-medical and/or it may have growth promotion effect (for example acidifiers, vegetable extracts, aromatic substances, growth factors, alone or mixed).

Therefore, this premix may be:

(1)—specific: zeolite only according to this invention on an ad hoc support, for example such as cereal by-products, calcium carbonate, corn cobs, other clays, alone or mixed;

(2)—partially specific: zeolite according to this invention+one or two other additives with effects comparable to those of zeolite, for example such as acidifiers, vegetable extracts, aromatic substances, growth factors alone or mixed, incorporated at doses less than their effective doses, on supports for example such as cereal by-products, calcium carbonate, corn cobs, other clays, alone or mixed;

(3)—non specific: zeolite according to this invention incorporated into a complete premix containing at least vitamins and trace elements.

In all cases, the premix is incorporated into the final food distributed to animals advantageously at rates usually varying from 500 g to 5 kg of premix per tonne of food.

This invention also relates to a supplemented food for animals, containing a food additive according to this invention or a premix according to this invention.

Advantageously, the supplemented food for animals according to this invention is such that the quantity of zeolite present is 5 to 200 ppm by weight as a proportion of the total weight of the food, advantageously between 5 and 100 ppm, advantageously between 5 and 80 ppm, even better between and 20 ppm, and advantageously equal to about 10 ppm by weight.

Finally, this invention relates to a method of improving the growth of animals, characterised in that it consists of incorporating a zeolite according to this invention into the food of the said animals, advantageously with a quantity of 5 to 200 ppm by weight as a proportion of the total weight of food, advantageously between 5 and 100 ppm, advantageously between 5 and 80 ppm, even better between 5 and 20 ppm, and advantageously equal to about 10 ppm by weight.

In one advantageous embodiment, the process according to this invention is such that the zeolite according to this invention is incorporated in the form of a food additive according to this invention or in the form of a premix.

Advantageously, the animals are chosen from among farm animals or pets, advantageously porcines (particularly pigs), bovines, ovines, goats, poultry (particularly chickens and turkeys), rabbits, fish and birds.

The beneficial effects of this food additive can be summarised as follows (on mammals, birds and fish):
increase animal growth,
and/or lower their consumption index (in other words the quantity of food necessary for one unit weight gain), and consequently increase their transformation index (in other words the weight gain possible per food unit).

The following examples illustrate the invention without limiting its scope.

EXAMPLE 1

Figure 1:
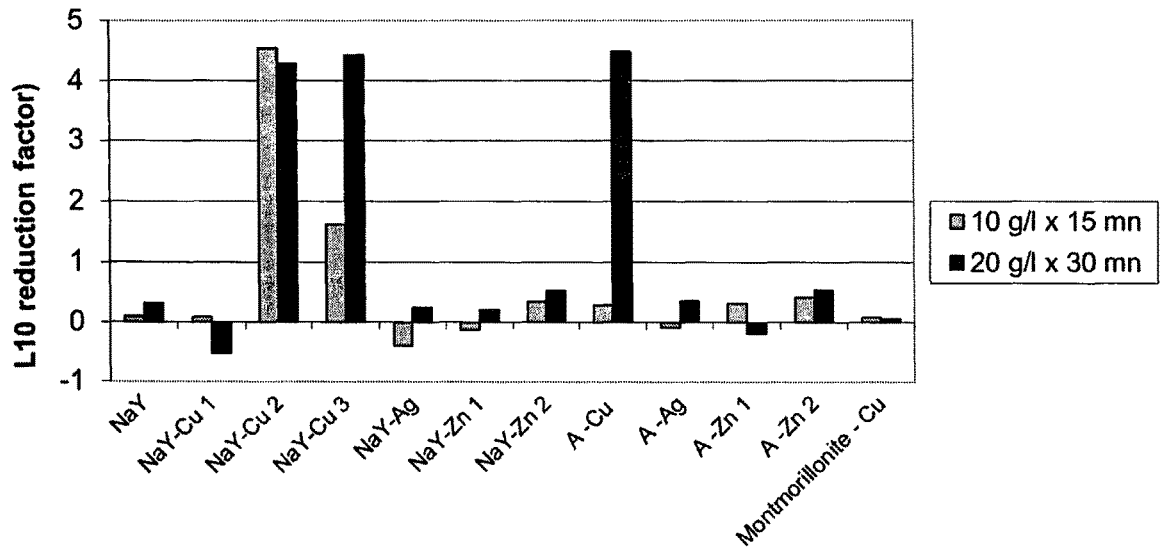
FIG. 1 represents the inhibiting activity of *Escherichia Coli* for different zeolites exchanged or not exchanged with copper, silver or zinc, and for montmorillonite exchanged with copper (doses of 10 grams per litre of zeolite for 15 minutes exposure or 20 grams per litre of zeolite for 30 minutes exposure).

Preparation of a Type Y Zeolite Containing 5.1% by Weight of $Cu^{2+}$ According to this Invention The initial NaY zeolite (before exchange) used has an Si/Al (atomic) ratio equal to 2.6 (x=2.6); its general formula is $NaAlO_2, 2.6 SiO_2, wH_2O$, the water representing the water absorbed in the zeolite pores (capillary condensation), that can be eliminated by increasing the temperature. Pores open at between 8 and 9 Å with a supercage at 13 Å.

$Na^+$ is exchanged by $Cu^{++}$ as follows:

The NaY zeolite in powder form is put into suspension while stirring in an aqueous solution (demineralised water) of $Cu^{++}$ copper nitrate (other salts such as sulphate may be suitable).

In this case, 200 g of zeolite is used in 0.5 litres of aqueous solution of copper sulphate (0.44 Molar), which is a V/P ratio of 2.5, a temperature of 70° C. and an exchange time of 3 hours.

The next step is to recover exchanged zeolite, which is bluish, by filtration and washing on a filter funnel and washing on a filter with percolation with two litres of demineralised water. The zeolite is then dried (in the drying oven at 120° C. over night), and the copper content measured by Inducted Conducted Plasma (ICP) (plasma torch emission spectroscopy) (dry at 400° C.)) is 5.2%. Therefore the exchange % is 40%.

EXAMPLES 2 TO 10

Preparation of a Type Y or A Zeolite Exchanged with Copper, Zinc or Silver According to this Invention The operating conditions and therefore the copper content can be varied. Table 1 given below represents the different operating conditions for examples 2 to 10 and zeolites according to this invention with the metal content obtained.

For all these examples, V/P=2.5, the exchange temperature is 60° C. and the exchange time is 3 hours.

| Example | Initial zeolite | Metallic salt | Concentration (molar) in metallic salt in the aqueous solution | Metal content in % by weight | % exchange |
|---|---|---|---|---|---|
| 2 | NaY | Copper sulphate | 0.05 | 2.35% Cu | 18 |
| 3 | NaY | Copper sulphate | 1 | 8.7% Cu | 68 |
| 4 | NaY | Zinc nitrate | 0.6 | 5% Zn | 37 |
| 5 | NaY | Silver nitrate | 0.01 | 0.2% Ag | 0.5 |
| 6 | NaY | Silver nitrate | 0.5 | 14.7% Ag | 37 |
| 7 | A | Copper sulphate | 0.5 | 9% Cu | 41 |
| 8 | A | Zinc nitrate | 0.6 | 5% Zn | 22 |
| 9 | A | Silver nitrate | 0.01 | 0.2% Ag | 0.3 |
| 10 | A | Silver nitrate | 0.5 | 12.5% Ag | 18 |

EXAMPLE 11

Preparation of a Type Y Zeolite Containing 3.3% by Weight of Copper According to this Invention The exchange between zeolite and the metallic salt can be made in the solid state.

Thus, 100 g of zeolite is intimately mixed in a mortar with 13 g of copper sulphate $Cu SO_4 5H_2O$. The mix is thus kept over night at ambient temperature.

The next step is washing with demineralised water (1 litre) on a filter funnel to extract non-exchanged copper.

The zeolite is then dried at 120° C.; the copper content (measured by ICP) is 3.3% by weight; the exchange rate is 25%.

The same is performed at 60° C. (instead of ambient temperature); the copper content is approximately the same, which is logical because in this case copper is practically entirely exchanged.

EXAMPLE 12

In Vivo Tests of NaY Zeolites According to this Invention Containing Between 5 and 6% by Weight of Copper in Different Animals The growth data and consumption index data (that illustrates the food efficiency, as being the food quantity necessary to obtain one kilogram of additional live weight—the consumption index is unitless by definition, since it is the ratio of two equivalent measurements) are indicated in indexed form; the control is indexed to 100, and the performances of experimental batches with zeolite are indexed with respect to this base. An index of 103.2 means a performance 3.2% better than the control performance.

Piglets

First piglet test: 192 piglets between 42 and 70 days old broken down into batches according to their live weight and receiving food corresponding to their physiological stage supplemented by variable quantities of NaY zeolite containing 6% by weight of copper according to this invention (0 ppm (control) 3, 6 or 12 ppm).

The average performances are given in table 2 below:

|  | control |  |  |  |
|---|---|---|---|---|
| Incorporation rate of zeolite according to this invention in ppm | 0 | 3 | 6 | 12 |
| Growth | 100 | 94.7 | 109 | 103.5 |
| Consumption index | 100 | 103.2 | 95.7 | 95.7 |

The incorporation of zeolite according to this invention gives an improvement in the growth of piglets between 42 and days old. This improvement can be modelled using a $2^{nd}$ degree equation that allows a maximum for a zeolite incorporation ratio according to this invention equal to between 9 and 10 ppm in proportion to the total weight of the food.

Second piglet test: 56 piglets from 21 to 42 days old weight, and receiving a food corresponding to their physiological stage, supplemented by variable quantities of NaY zeolite containing 6% by weight of copper according to this invention (0 ppm (control) 5, 10 or 20 ppm).

The average performances are given in table 3 below:

|  | control |  |  |  |
|---|---|---|---|---|
| Incorporation rate of zeolite according to this invention in ppm | 0 | 5 | 10 | 20 |
| Growth | 100 | 114.6 | 116.4 | 110.4 |

The incorporation of zeolite according to this invention gives an improvement in the growth of piglets between 21 and days old. This improvement can be modelled using a $2^{nd}$ degree equation that allows a maximum for a zeolite incorporation ratio according to this invention equal to about 12 ppm in proportion to the total weight of the food.

Third piglet test: 56 piglets from 21 to 42 days old, and then from 42 to 70 days old broken down into batches according to their live weight, and receiving a food corresponding to their physiological stage, supplemented by variable quantities of NaY zeolite containing 6% by weight of copper according to this invention (2.8 ppm (control) 5, 7.2 or 11.6 ppm).

The average performances are given in table 4 below:

|  | control |  |  |  |
|---|---|---|---|---|
| Incorporation rate or zeolite according to this invention in ppm | 2.8 | 5 | 7.2 | 11.6 |
| Growth | 100 | 105.5 | 109.7 | 108.9 |

The incorporation of zeolite according to this invention gives an improvement in the growth of piglets between 21 and days old. This improvement can be modelled using a 2nd degree equation that allows a maximum for a zeolite incorporation ratio according to this invention equal to between 9 and 10 ppm in proportion to the total weight of the food.

Chickens 660 chickens from 1 to 28 days old broken down into batches according to their live weight, and receiving a food corresponding to their physiological stage, supplemented by variable quantities of NaY zeolite containing 6% by weight of copper according to this invention (0 ppm (control) 5, 10 or 20 ppm).

The average performances are given in table 5 below:

|  | control |  |  |
|---|---|---|---|
| Incorporation rate of zeolite according to this invention in ppm | 0 | 6 | 15 |
| Growth | 100 | 105.4 | 104.5 |

The incorporation of zeolite according to this invention gives a small improvement in the growth of chickens between 1 and 28 days old.

Turkeys 360 turkeys from 28 to 55 days old broken down into batches according to their live weight, and receiving a food corresponding to their physiological stage, supplemented with 5 ppm of NaY zeolite containing 6% by weight of copper according to this invention or 0 ppm (control).

The average performances are given in table 6 below:

|  | Weight D28 gram | Weight D55 gram | Weight gain gram | Consumption for period gram | Consumption index |
|---|---|---|---|---|---|
| Control | 990 | 3077 | 2087 | 4357 | 2.09 |
| Zeolite according to this invention 5 ppm | 996 | 3235 | 2239 | 4440 | 1.97 |
| Statistical sign. |  | p < 0.001 | p < 0.001 |  | p < 0.001 |

The incorporation of zeolite according to this invention gives a very significant improvement in the growth of turkeys between 28 and 55 days old.

EXAMPLE 13

In Vitro Test of Zeolites According to this Invention on Different Micro Organisms The methodology used is based on the measurement of the bactericide activity of zeolite according to this invention in a liquid medium, and is comparable regardless of the micro organism being tested. The principle is as follows:

preparation of a suspension of bacteria with $10^8$ or $10^9$ germs per ml 50 ml of this suspension is put into contact with quantity of zeolite according to this invention, and stirring for a given time;

numbering of germs remaining after treatment.

Each dose x time pair includes its own control.

Results are expressed as a reduction factor of the initial colony (number of control germs divided by the number of germs after treatment).

Interest, Specific Nature of the Metallic Ion and Specific Nature of Zeolite

The average reducing activity was calculated as being the quotient of the average reduction expressed in log 10, by the average value of the exposure (dose x time).

Different zeolites were tested:

A non-exchanged zeolite (NaY), NaY zeolites exchanged with copper containing 2.3% by weight of copper according to example 2 (NaY—Cu1: exchange rate 18%), 8.7% by weight of copper according to example 3 (NaY—Cu2: exchange rate 68%) and 10% by weight of copper (NaY—Cu3: exchange rate 78%), an NaY zeolite exchanged with silver containing 14.7% by weight of silver according to example 6 (NaY—Ag: exchange rate 37%), NaY zeolites exchanged with zinc containing 5.2% by weight of zinc (NaY—Zn1: exchange rate 38%) and 5% by weight of zinc according to example 4 (NaY—Zn2: exchange rate 37%), an A zeolite exchanged with copper containing 8.9% by weight of copper (A-Cu: exchange rate 41%), an A zeolite exchanged with silver containing 12.5% by weight of silver according to example 10 (A-Ag: exchange rate 18%), A zeolites exchanged with zinc containing 8.4% by weight of zinc (A—Zn1: exchange rate 38%) and 8% by weight of zinc (A-Zn2: exchange rate 36%) and montmorillonite exchanged with copper as described in Chinese publications (Xia et al., 2004 Poultry Science 83: 1868-1875, Xu et al., *Asian-Aust. J. Anim. Sci.* 2003 Vol 16, No. 11: 1673-1679, Xia et al., *Asian-Aust. J. Anim. Sci.* 2004. Vol 17, No. 12: 1712-1716 and Hu et al., *Asian-Aust. J. Anim. Sci.* 2004 Vol 17, No. 11: 1575-1581).

Figure 2:
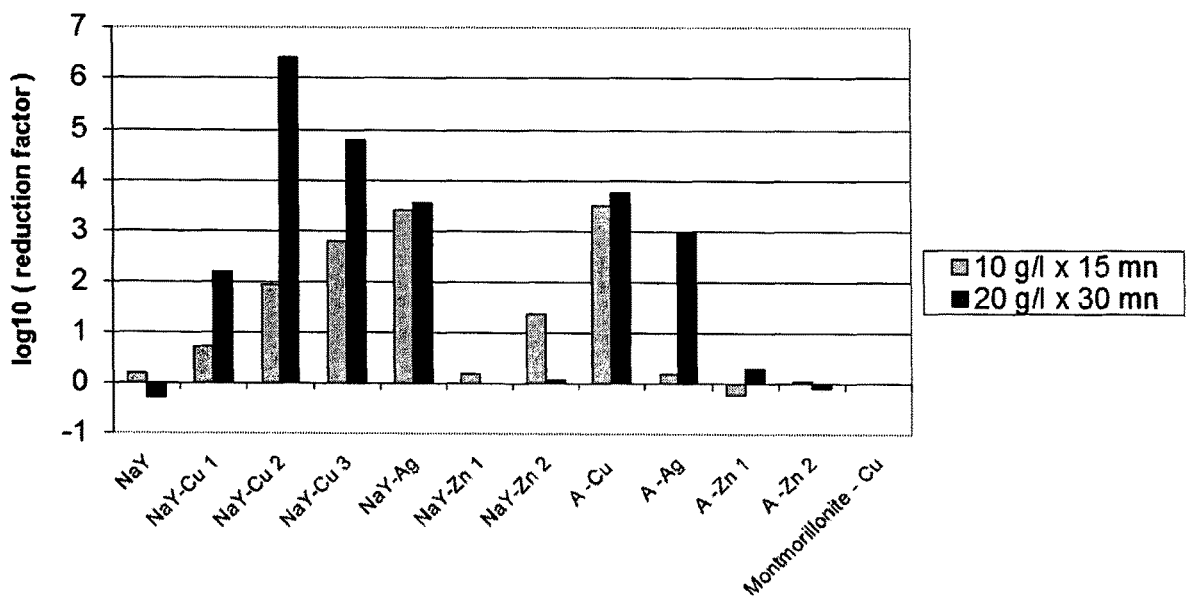
FIG. 2 represents the inhibiting activity of *Clostridium sporogenes* for different zeolites exchanged or not exchanged with copper, silver or zinc, and for montmorillonite exchanged with copper (doses of 10 grams per litre of zeolite for 15 minutes exposure or 20 grams per litre of zeolite for 30 minutes exposure).

FIGS. 1 and 2 illustrate the average reducing activity of these zeolites on *E. Coli* and *C. Sporogenes*. Thus, note:

the lack of activity of native zeolite (Nay vs Nay-Cu)
the intermediate activity of Nay-Ag (exchange with silver)
the activity of zeolite A exchanged with copper or silver
the very low activity of montmorillonite exchanged with copper.

The invention claimed is:

1. A premix of non-medical growth promoter food additive for animals containing a non-medical food additive on a support and/or in combination with at least another animal food additive, wherein the non-medical food additive is an animal growth promoter containing 99% pure type Y zeolite partially or totally exchanged with a $C^{m+}$ cation with the general formula I below:

$$\frac{1}{m}yC^{m+}(1-y)\frac{1}{n}M^{n+}AlO_2xSiO_2$$

in which x is greater than 1;
$M^{n+}$ represents an alkaline or alkaline earth exchangeable ion;
n is 1 or 2;
y is the exchange rate and is between 0.001 and 1;
$C^{m+}$ is $Cu^{2+}$;
m is 2,
and wherein the zeolite contains between 3 and 9% by weight of copper as a proportion of the total weight of zeolite.

2. The premix according to claim 1, wherein y is between 0.01 and 0.80.

3. The premix according to claim 1, wherein the zeolite contains between 5 and 6% by weight of copper as a proportion of the total weight of zeolite.

4. The premix according to claim 1, wherein x is 2.6.

5. The premix according to claim 1, wherein $M^{n+}$ is $Na^+$.

6. The premix according to claim 1, wherein y is between 0.1 and 0.5.

7. The premix according to claim 1, wherein the support and/or the other animal food additive is selected from the group consisting of cereal by-products, calcium carbonate, corn cobs, clays, acidifiers, vegetable extracts, aromatic substances, growth factors, vitamins, trace elements, and mixtures thereof.

8. A supplemented food for animals containing a non-medical food additive, wherein the non-medical food additive is an animal growth promoter containing 99% pure type Y zeolite partially or totally exchanged with a $C^{m+}$ cation with the general formula I below:

$$\frac{1}{m}yC^{m+}(1-y)\frac{1}{n}M^{n+}AlO_2xSiO_2$$

in which x is greater than 1;
$M^{n+}$ represents an alkaline or alkaline earth exchangeable ion;
n is 1 or 2;
y is the exchange rate and is between 0.001 and 1;
$C^{m+}$ is $Cu^{2+}$;
m is 2,
and wherein the zeolite contains between 3 and 9% by weight of copper as a proportion of the total weight of zeolite.

9. The supplemented food according to claim 8, wherein y is between 0.01 and 0.80.

10. The supplemented food according to claim 8, wherein the zeolite contains between 5 and 6% by weight of copper as a proportion of the total weight of zeolite.

11. The supplemented food according to claim 8, wherein x is 2.6.

12. The supplemented food according to claim 8, wherein $M^{n+}$ is $Na^+$.

13. The supplemented food according to claim 8, wherein y is between 0.1 and 0.5.

14. The supplemented food according to claim 8, wherein the quantity of zeolite present is 5 to 200 ppm by weight as a proportion of the total weight of the food.

15. The supplemented food according to claim 8, wherein the quantity of zeolite present is equal to about 10 ppm by weight as a proportion of the total weight of the food.

16. A supplemented food for animals, containing a premix according to claim 1.

17. A method of improving the growth of an animals comprising administering to the animal a food comprising a 99% pure type Y zeolite partially or totally exchanged with a $C^{m+}$ cation with the general formula I below:

$$\frac{1}{m}yC^{m+}(1-y)\frac{1}{n}M^{n+}AlO_2xSiO_2$$

in which x is greater than 1;
$M^{n+}$ represents an alkaline or alkaline earth exchangeable ion;
n is between 1 or 2;
y is the exchange rate and is between 0.001 and 1;
$C^{m+}$ is $Cu^{2+}$;
m is 2,
and wherein the zeolite contains between 3 and 9% by weight of copper as a proportion of the total weight of zeolite.

18. The method according to claim 17, wherein the animals are selected from the group consisting of porcines, bovines, ovines, goats, poultry, rabbits, fish and birds.

19. The method according to claim 17, wherein the zeolite is incorporated in the food of said animals with a quantity of 5 to 200 ppm by weight as a proportion of the total weight of food.

20. A method of improving the growth of an animals comprising administering to the animal the premix according to claim 1.

21. A premix of non-medical growth promoter food additive for animals containing a non-medical food additive and another ingredient selected from among the group consisting of cereal by-products, calcium carbonate, corn cobs, vegetable extracts, growth factors, vitamins, trace elements, aromatic substances, and mixtures thereof,
wherein the non-medical food additive is an animal growth promoter containing 99% pure type Y zeolite partially or totally exchanged with a $C^{m+}$ cation with the general formula I below:

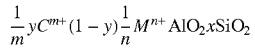

in which x is greater than 1;
$M^{n+}$ represents an alkaline or alkaline earth exchangeable ion;
n is 1 or 2;
y is the exchange rate and is between 0.001 and 1;
$C^{m+}$ is $Cu^{2+}$;
m is 2,
and wherein the zeolite contains between 3 and 9% by weight of copper as a proportion of the total weight of zeolite.

* * * * *